United States Patent
Denny et al.

[11] Patent Number: 6,047,209
[45] Date of Patent: Apr. 4, 2000

[54] METHOD AND APPARATUS FOR MAINTENANCE OF PIERCED ORIFICES

[76] Inventors: Jeffrey Paul Denny, 570 Carpenteria Rd.; Mark A. Boys, 412 Carpenteria Rd., both of Aromas, Calif. 95004

[21] Appl. No.: 09/285,427

[22] Filed: Apr. 2, 1999

[51] Int. Cl.[7] ............................... A61N 1/30; A61M 1/00
[52] U.S. Cl. ................................ 604/21; 604/27; 604/37; 604/43; 604/47; 604/49
[58] Field of Search .................................. 604/21, 19, 27, 604/28, 36, 37, 43, 46, 48, 51, 49, 47

[56] References Cited

U.S. PATENT DOCUMENTS

| | | | |
|---|---|---|---|
| 5,352,192 | 10/1994 | Byrne et al. | 604/20 |
| 5,810,763 | 9/1998 | Feiring | 604/21 |

*Primary Examiner*—Gary Jackson
*Attorney, Agent, or Firm*—Donald R. Boys, Central Coast Patent Agency

[57] ABSTRACT

A needle for use with an apparatus for injecting fluid into a pierced body orifice has a hollow body having an axis and an internal bore along the axis, a blunt, closed first end, an open second end with an interface to a closure for attachment to a reservoir, and one or more side openings at substantially a right angle to the axis communicating from the internal bore to outside the hollow body. The needle may be curved or straight. A fluid injection system based on the needle uses such as squeeze bottles or syringes to express material through the needle. In another aspect a treatment apparatus for treatment of a pierced body orifice has a hollow body having an inner bore and first openings through walls of the body from the inner bore to outside the body, a reservoir communicating with the inner bore of the hollow body via at least one second opening in the hollow body; and an expression mechanism whereby volume of the reservoir may be reduced, expressing fluid from the reservoir through the second opening and the inner bore, and out of the first openings. Various expression mechanisms are usable.

5 Claims, 4 Drawing Sheets

METHOD AND APPARATUS FOR MAINTENANCE OF PIERCED ORIFICES

FIELD OF THE INVENTION

The instant invention is in the area of infection-prevention and treatment apparatus, and relates more particularly to jewelry adapted to aid in preventing and treating infections in orifices of pierced human body parts.

BACKGROUND OF THE INVENTION

The art of body piercing has increased dramatically in the past decade. Pierced orifices were previously confined to just the human earlobes. Today, pierced orifices have become a rite of passage for many teenagers and young adults. Pierced areas range from the earlobes, belly button, nose, nipples, genitalia, to eyebrows, lips and tongues. The current method of art uses a specialized instrument called a piercing gun, which shoots a sterilized post or ring into and through the skin or body part. The current method to reduce infection in body-piercing practice is to apply an antibiotic ointment with a cotton swab a few days after the original piercing. Cleaning the earrings or other body rings with alcohol and turning them frequently so they do not stick is also recommended. The conventional wisdom is that the rings should not be removed for four to six weeks after the piercing to prevent the holes from closing.

The current method of cleaning a pierced orifice is to swab newly pierced areas twice a day with antiseptic hydrogen peroxide, then dab on an antibiotic ointment such as Polysporin. After about a week, soap and water is thought to be sufficient.

During the first 30 days after the piercing, it is critical to watch for possible infections and allergies. Irritations often result from a sensitivity to nickel and other metals found in inexpensive jewelry. Symptoms of infection can include a discharge or redness in the pierced area and will, in some cases, require medical attention. Pierced orifices in the genital area can be especially dangerous as they will frequently come in contact with urine and/or fecal matter. Nose pierces can also be sites of bacterial growth and require special care. For example, a nose pierce requires careful cleaning with alcohol and must be watched for infection. Nose rings should be removed if one develops a cold or congestion.

With these current methods of piercing maintenance, it is recommended that a person remove earrings at the first sign of redness, swelling, crusting or oozing, and wash effected areas with soap and water. If the redness and swelling persists after a day or two, it is recommended that the person use hydrogen peroxide and antibiotic ointment treatment. If the trouble doesn't clear up within a few days it could lead to a more generalized infection. If the ring is left in too long during the infection, the inflamed tissue can grow over the inner end of the ring making it very painful to remove the ring.

The prior art practice does not effectively reduce infection within the pierced orifice, only around it. The only method suggested for cleaning or disinfecting the inside of a newly pierced orifice is the application of substances on the jewelry using a cotton swab and then rotating the ring or bar to attempt to get the substance into the inside of the orifice. The problem with this method is that the human skin often acts like a squeegee, thereby preventing the substance from effectively entering the interior of the pierced orifice. Also, since for the first four to six weeks, the original ring should not be removed as not to have the orifice close, using a method that would clean the inside of the pierced orifice without removing the ring would promote faster healing reducing risk of infection.

Further, while it is most critical to prevent infection during the first 4 to 6 weeks after the piercing, it is also important to continue, after this initial period, a regimen of keeping the pierced orifices clean, especially those located in areas where bacteria growth and infection might be more likely. Infection, allergic reaction or irritation can arise at anytime due to different metals in rings, the weight of rings and not properly keeping the pierced orifices cleaned.

What is clearly needed in the art are methods and apparatus for ongoing application of an infection-reducing and cleansing substance from the inside of a pierced orifice thereby maintaining a clean and infection-free environment that is both medically and psychologically beneficial.

SUMMARY OF THE INVENTION

In a preferred embodiment of the present invention a cannula or needle (hereafter referred to as a needle) for use with an apparatus for injecting fluid into a pierced body orifice is provided, comprising a hollow body having an axis and an internal bore along the axis; a blunt, closed first end; an open second end with an interface to a closure for attachment to a reservoir; and one or more side openings at substantially a right angle to the axis communicating from the internal bore to outside the hollow body. The needle body and axis may be curved and may be of size and diameter that approximates the size of an earring or any body jewelry typically used with pierced human orifices.

In another aspect a fluid injection system for injecting fluid into a pierced body orifice is provided, comprising a needle, a hollow body having an axis and an internal bore along the axis, a blunt, closed first end, an open second end with an interface to a closure for attachment to a reservoir, and one or more side openings at substantially a right angle to the axis communicating from the internal bore to outside the hollow body; and a collapsible, flexible reservoir mounted to the needle interface such that collapsing the reservoir forces fluid in the reservoir through the internal bore of the needle and out the one or more side openings. The reservoir may be a plastic squeeze bottle or a syringe, and the needle may be curved.

In yet another aspect a treatment ring for treatment of a pierced body orifice is provided, the treatment ring comprising a hollow body having an inner bore and first openings through walls of the body from the inner bore to outside the body; a reservoir communicating with the inner bore of the hollow body via at least one second opening in the hollow body; and an expression mechanism whereby volume of the reservoir may be reduced, expressing fluid from the reservoir through the second opening and the inner bore, and out of the first openings. The expression mechanism may comprise a threaded cap engaging a threaded bore in a body of the reservoir, or a squeeze bottle or a syringe.

In yet another embodiment a method for treating and maintaining a pierced body orifice is provided, comprising steps of (a) inserting a ring in the pierced orifice, the ring having a curved hollow body having an inner bore and first openings through walls of the body from the inner bore to outside the body, a reservoir communicating with the inner bore of the hollow body via at least one second opening in the hollow body, and an expression mechanism whereby volume of the reservoir may be reduced, expressing fluid from the reservoir through the second opening and the inner bore, and out of the first openings; and (b) periodically operating the expression mechanism to express a treatment fluid from the reservoir into the pierced body orifice. In the above embodiments the ring can be a straight bar or post as well as a ring.

In embodiments of the present invention for the first time, apparatus is provided for effective treatment and management of pierced body orifices, so infections and allergic reactions may be prevented or treated and controlled. This apparatus and methods of practice are described in enabling detail below.

BRIEF DESCRIPTION OF THE DRAWING FIGURES

DESCRIPTION OF THE PREFERRED EMBODIMENTS

In a first preferred embodiment of the invention a hand-held apparatus is provided for easy daily cleaning and maintenance of a pierced orifice after the initial four to six weeks have passed since initial piercing. The apparatus comprises a bottle or reservoir that can be made of a number of different materials. A cleaning material, which can be salve, hydrogen peroxide, Polysporin or any number of antibiotic or cleaning fluids, is stored in the bottle. A blunt needle is attached to the bottle, and is of a size and shape adapted to enter into any pierced orifice on the body. The needle has small holes exiting the hollow needle at right angles to the bore of the needle, and the needle is closed on the end away from the bottle, which allows the fluid in the bottle to be distributed into the interior of the desired orifice. When the bottle is squeezed, the action sends the fluids up through and out of the needle openings directly into the pierced orifice.

Figure 1:
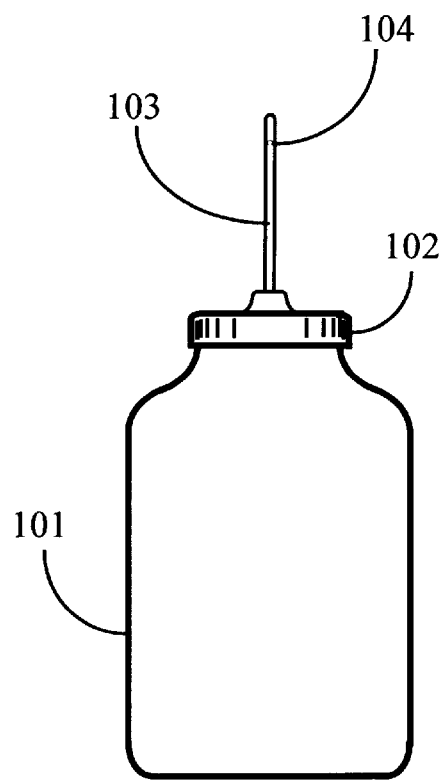
FIG. 1 is an elevation view of a squeeze bottle and orifice needle in an embodiment of the present invention.

Referring to FIG. 1, a small, hand-held squeeze bottle 101 with a blunt, straight needle 103 can be used for the maintenance of pierced orifices during or after the initial four to six week healing period. The squeeze bottle can be made of a number of suitable flexible materials such as a plastic substance, which allows a user to expel the fluid or salve in the bottle such as by squeezing the bottle. The fluids can be hydrogen peroxide, soap and water, saline solution or a topical antibiotic, for example. When the bottle is squeezed the fluid is expressed from the bottle through the needle to the inside the orifice via side-opening holes illustrated by hole 104. There may be one or several such sideopening holes. Flushing a pierced orifice with fluid or applying salve from the bottle can reduce or prevent infection by flushing out or killing bacteria that may build up inside the orifice. This treatment can also reduce adverse reactions to different kinds of metals used in the orifice rings or bars. Cap 102 shown in FIG. 1 is adapted to hold the blunt needle and prevents fluid from spilling out from the bottle when the bottle is squeezed forcing fluid into the blunt needle.

Needle 103, as shown in FIG. 1, has small holes exiting at right angles to the needle bore on either side of the needle or near the end of the needle, and is open on the end opposite the blunt, closed end. At the open end the needle is implemented to interface with a cap or other device for attaching to the squeeze bottle or other reservoir. The interface can be such as a shoulder or flange, or may just be the exterior surface of the needle which may pass through a seal, such as an o-ring or the like. In practice the needle is placed inside the orifice and the fluid is squeezed directly inside the pierced orifice through the holes in the needle. The needle can be made of a number of materials such as surgical steel or any other suitable material. The holes in the needle can be placed anywhere along the length of the needle depending on the type of orifice that needs to be cleaned.

Figure 2:
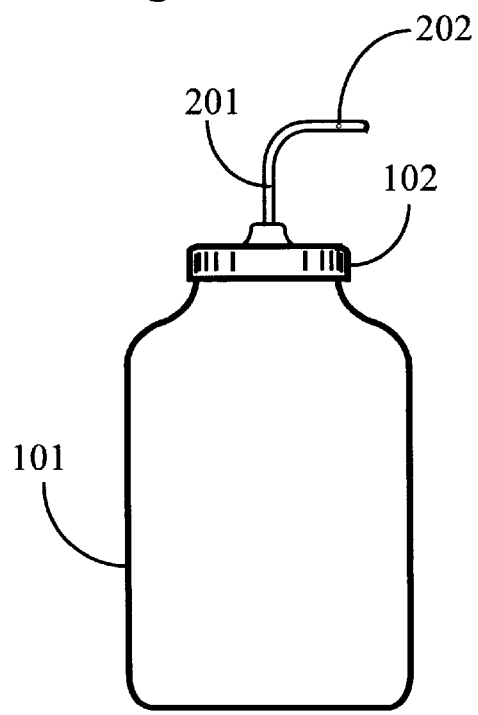
FIG. 2 is the elevation view of FIG. 1 having a curved needle.

FIG. 2 is an elevation view illustrating an alternative embodiment of the present invention comprising a cap 102, a bottle or reservoir 101, a curved needle or cannula 201 and at least one hole 202. As shown in FIG. 2 blunt needle 201 can be of various sizes and curvatures to emulate piercing rings, bars or posts for various purposes. The needle can also be removable from the squeeze bottle so that it allows for easy cleaning, sterilization or replacing solution or salve, and for cleaning and sterilizing the needle after each application. Side openings 202 in FIG. 2 are analogous to openings 104 of FIG. 1.

Figure 3:
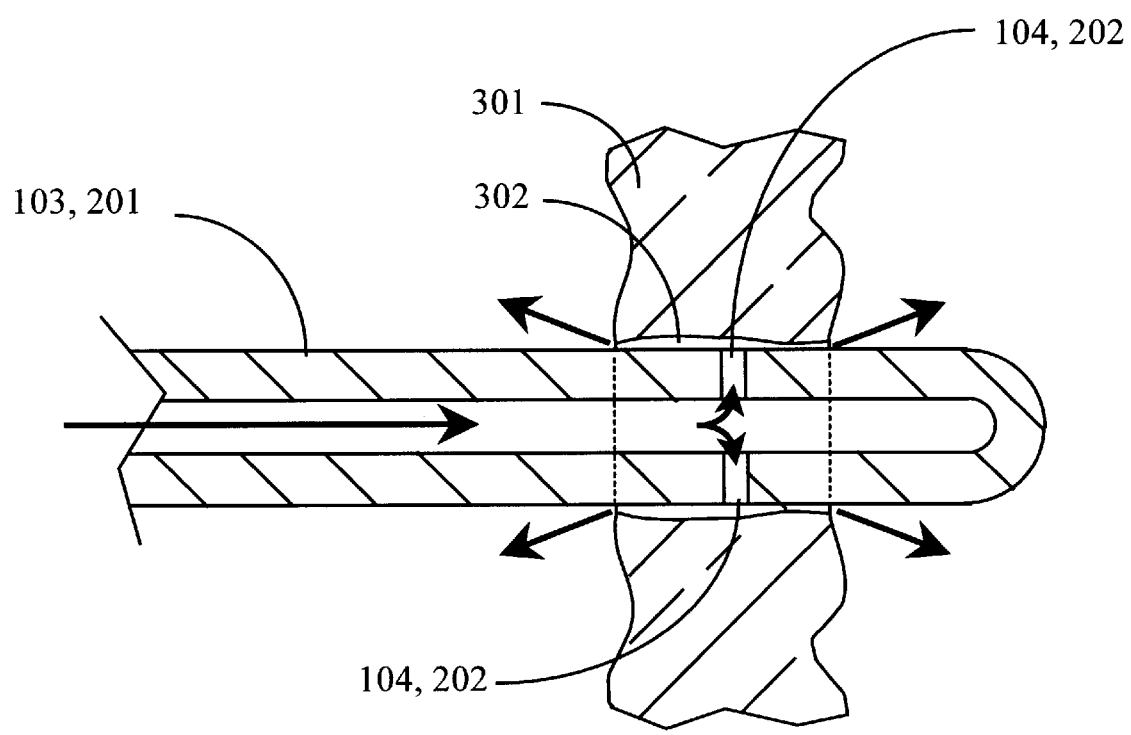
FIG. 3 is a magnified view illustrating practice of the invention using the apparatus of FIG. 1 and FIG. 2.

FIG. 3 is a magnified view illustrating practice of the invention comprising blunt needle or cannula 103 or 201, body part 301, orifice interior 302 and openings or holes 104 or 202. This embodiment uses the apparatus of FIG. 1 and FIG. 2. As shown in FIG. 3, the blunt needle can be designed for fluid to be dispersed from different areas on the needle depending on the location and type of piercing to be cleaned. FIG. 3 shows a blunt needle 103 or 201 having side openings 104 or 202 inserted in a pierced orifice 302 through a body part 301. The squeeze bottle is not shown in FIG. 3, but the skilled artisan will understand that squeezing the bottle will force fluid or salve through the internal bore of needle 103 or 201 and out the side-holes into pierced orifice 302, effectively flushing the orifice and leaving fluid or salve in the orifice when the blunt needle is removed.

In another aspect of the invention a hollow first ring, bar or post is provided to reduce infection and allergic reactions during the first critical four to six weeks after making a pierced orifice. The ring or post can be made of a number of materials like surgical steel or any other suitable material, and may have a number of tiny holes to allow fluid or salve to be distributed into the pierced orifice. It can be placed in the pierced orifice and remain there for the full four to six weeks or remain as a permanent article of jewelry. A reservoir attached to a base of the ring or post holds the necessary fluid or salve to be used to clean the pierced orifice. A knob or plunger integrated with the reservoir allows the fluid to be manually expressed into the orifice as often as needed to effect treatment.

Figure 4:
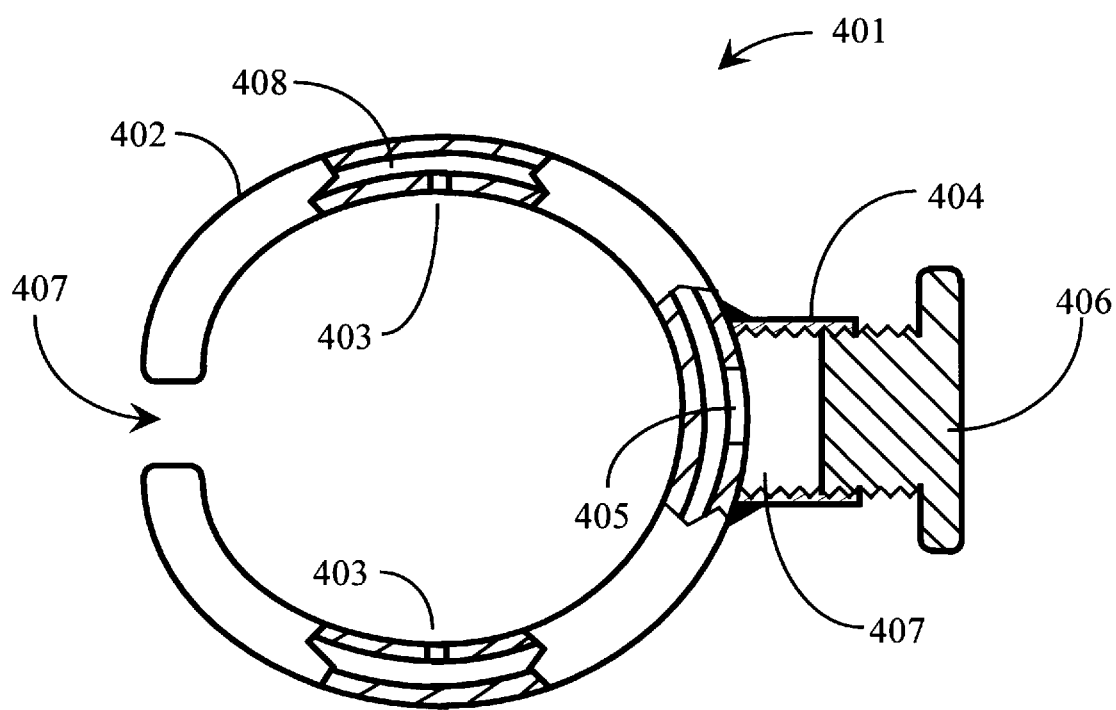
FIG. 4 is a partially sectioned view of a hollow ring in an embodiment of the present invention.

FIG. 4 is a partially-sectioned view of a hollow ring in an embodiment of the present invention, useful primarily for a first critical period in treatment of a pierced orifice to avoid or treat infection and allergic reactions.

Ring 401 as shown in FIG. 4 has a body 402 that is made of a suitable material such as surgical steel, having a bore 408, which can easily be placed through a piercedorifice. Holes 403 in the ring allow the fluid or salve to exit hollow body 402 to be directly into the inside of the pierced orifice. The fluid is kept in a reservoir 407 in a base 404, the reservoir communicating with bore 408 of hollow body 402 through an internal opening 405. Fluid or salve is ejected from reservoir 407 in base 404 by turning a knob 406 threaded into base 404. The fluid is dispersed manually by turning the knob. The reservoir can be opened by removing knob 406 to refill the reservoir with whatever fluid is preferred. Knob 406 in the above embodiment can emulate a precious gem or other attractive decoration. Further, although a ring is shown in FIG. 4, the form may be of a straight bar or ring with any degree of curvature.

It will be apparent to those with skill in the art that the hollow ring of FIG. 4 may be implemented in several different ways. The ring can open in different ways at different points, for example, and the diameters of the bodies and bores can vary considerably depending on need. The body may be a straight bar rather than a ring. Moreover, the ejection holes (403) can vary in number, can have different diameters, and may be placed in the body in a variety of positions. In addition, the reservoir can vary in size, and the ejection mechanism (an exemplary threaded knob is shown) may be implemented in different ways. This mechanism could, for example, comprise a flexible membrane over the reservoir. There are many such possibilities within the spirit and scope of the invention.

Figure 5:
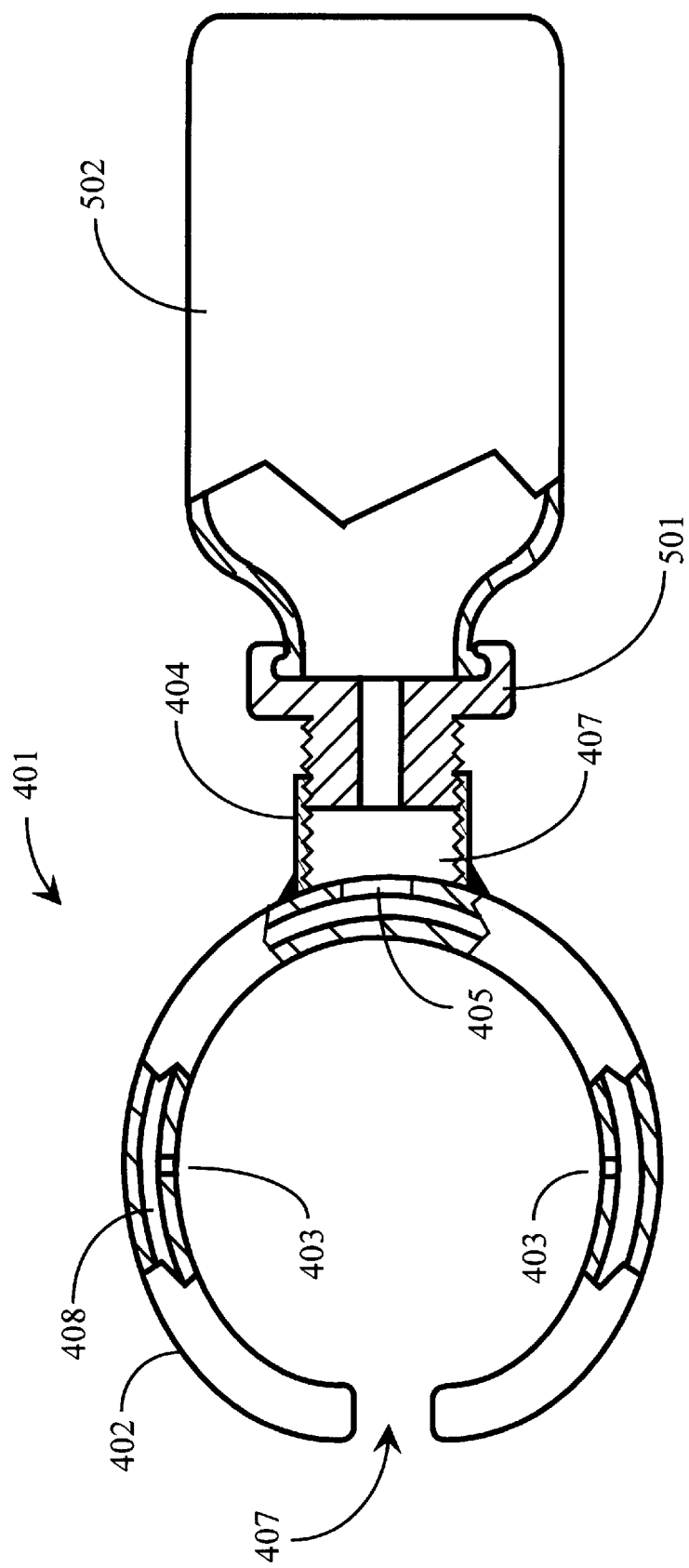
FIG. 5 illustrates an alternative embodiment using the ring of FIG. 4.

In another embodiment the hollow first ring 401 of FIG. 4 may be used with a squeeze bottle or other larger reservoir to allow for fluid of salve to be expressed into the pierced orifice alternatively to the smaller manipulatable reservoir 407. FIG. 5 illustrates a ring 401 with a special cap 501 for engaging a squeeze bottle 502. A use of this alternative may be for example, in a situation wherein the ring itself is charged in reservoir 407 with a salve, and the salve is expressed into the pierced orifice on a periodic schedule for routine maintenance. At extended periods it may be desirable to irrigate the orifice with a fluid cleanser, washing away the salve and cleaning the orifice. For this purpose one may remove knob 406 and connect squeeze bottle 502 by means of screw cap 501, then irrigate the orifice with the cleansing fluid in the bottle. After irrigation, one may then remove cap 501, refill reservoir 407 with salve, and then replace knob 406 and rotate until salve is again in place in the pierced orifice. There may also be separate reservoirs for the salve and cleansing fluid in the same apparatus, or other ports whereby the cleansing fluid is applied via a bottle 502 and a needle through a separate port in the body of ring 402.

It will be apparent to the skilled artisan that there are many alterations that may be made in the embodiments described herein without departing from the spirit and scope of the invention. For example, squeeze bottles may be replaced by syringes and the like and such larger reservoirs may take many forms and may number more than one. Further rings such as 402 may take many diverse forms, as is described above. Materials may vary widely as well, and size, number, and placement of holes may vary. There are many such alterations within the spirit and scope of the invention. The invention, therefore, is limited only by the claims which follow.

What is claimed is:

1. A treatment apparatus for treatment of a pierced opening through body tissue, the treatment apparatus comprising:

an elongated hollow body having a first region for residing in the pierced opening and a second region for extending outside the pierced opening, an inner bore extending through a portion of the first and second regions, the inner bore comprising a first volume, and at least one passage in the first region through a wall of the body from the inner bore to outside the body;

a reservoir contiguous with the hollow body in the second region and opening to the inner bore of the hollow body, the reservoir comprising a second volume substantially greater than the first volume; and an expression mechanism interfaced to the reservoir whereby volume of the reservoir may be incrementally reduced, thereby expressing fluid from the reservoir into and through the inner bore, and out through the at least one passage in the first region through the wall of the body, and into the pierced opening.

2. The treatment apparatus of claim 1 wherein the expression mechanism comprises a threaded cap engaging a threaded bore in a body of the reservoir.

3. The treatment apparatus of claim 2 further comprising a squeeze bottle or syringe having a threaded closure with a thread compatible with and enraged in the threaded bore of the body of the reservoir.

4. The treatment apparatus of claim 2 wherein the threaded cap of the expression mechanism comprises a decorative ornament.

5. A method for treating and maintaining a pierced opening in body tissue, comprising steps of:

(a) inserting an apparatus in the pierced opening, the apparatus having a hollow body having an inner bore and first openings through walls of the body from the inner bore to outside the body, a reservoir communicating with the inner bore of the hollow body via at least one second opening in the hollow body, and an expression mechanism whereby volume of the reservoir may be reduced, expressing material from the reservoir through the second opening and the inner bore, and out of the first openings; and (b) periodically operating the expression mechanism to express a treatment fluid from the reservoir into the pierced opening in the body tissue.

* * * * *